(12) United States Patent
Hill et al.

(10) Patent No.: US 7,393,992 B2
(45) Date of Patent: Jul. 1, 2008

(54) METHOD FOR WORKING UP CRUDE 1,3-BUTADIENE

(75) Inventors: Thomas Hill, Ludwigshafen (DE); Klaus Kindler, Harthausen (DE); Bernd Heida, Ellerstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 577 days.

(21) Appl. No.: 10/522,194

(22) PCT Filed: Jul. 23, 2003

(86) PCT No.: PCT/EP03/08044

§ 371 (c)(1), (2), (4) Date: Jan. 24, 2005

(87) PCT Pub. No.: WO2004/011407

PCT Pub. Date: Feb. 5, 2004

(65) Prior Publication Data

US 2005/0240071 A1    Oct. 27, 2005

(30) Foreign Application Priority Data

Jul. 24, 2002  (DE)  ................................ 102 33 621

(51) Int. Cl.
*C07C 7/08*  (2006.01)

(52) U.S. Cl. ........................ 585/809; 585/810; 208/347; 208/74

(58) Field of Classification Search ................. 585/809, 585/810; 208/347; 203/74
See application file for complete search history.

(56) References Cited

U.S. PATENT DOCUMENTS 3,436,438 A * 4/1969 Hiroshi et al. ................. 203/9

(Continued)

FOREIGN PATENT DOCUMENTS

DE    198 18 810    10/1999

*Primary Examiner*—Tam M. Nguyen
(74) *Attorney, Agent, or Firm*—Oblon, Spivak, McClelland, Maier & Neustadt, P.C.

(57) ABSTRACT

Sudstituted the abstract with a new abstract as follows: The invention relates to a continuous process for separation a mixture of hydrocarbons which has beenobtained by extractive distillation of $C_4$ fraction useing a selective solvent and the hydrocarbons from the fraction $C_4$ which are more readily soluble in the selective solvent than are the butanes and the butenes. The mixture is fed into a first distillation column in which it is separated into a steam which is taken off at the top and comprises 1,3-butadiene, propyne, possibly further low boilers and possibly water and a bottom stream comprising 1,3-butadiene, 1,2-butadiene, acetylenes and possibly further high boilers, with the proportion of 1,3-butadiene in the bottom stream from the distillatin column being regulated in such a way that it is at least sufficiently high to dilute the acetylenes to outside the range in which there is a risk of spontaneous decomposition. The stream taken off from the top of the first distillation column is fed to a second distillation column and is separated into a steam which is taken off at the top and comprises propyne, possibly further low boilers and possibly water and a bottom stream comprising pure 1,3-butadiene in the second distillation column.

4 Claims, 1 Drawing Sheet

U.S. PATENT DOCUMENTS

| | | |
|---|---|---|
| 4,049,742 A | 9/1977 | Weitz et al. |
| 4,277,313 A * | 7/1981 | Mehra et al. .................. 203/32 |
| 6,337,429 B1 | 1/2002 | Kindler et al. |
| 6,376,735 B1 * | 4/2002 | Lankton ...................... 585/809 |
| 6,395,953 B1 * | 5/2002 | Koga et al. .................. 585/833 |

* cited by examiner

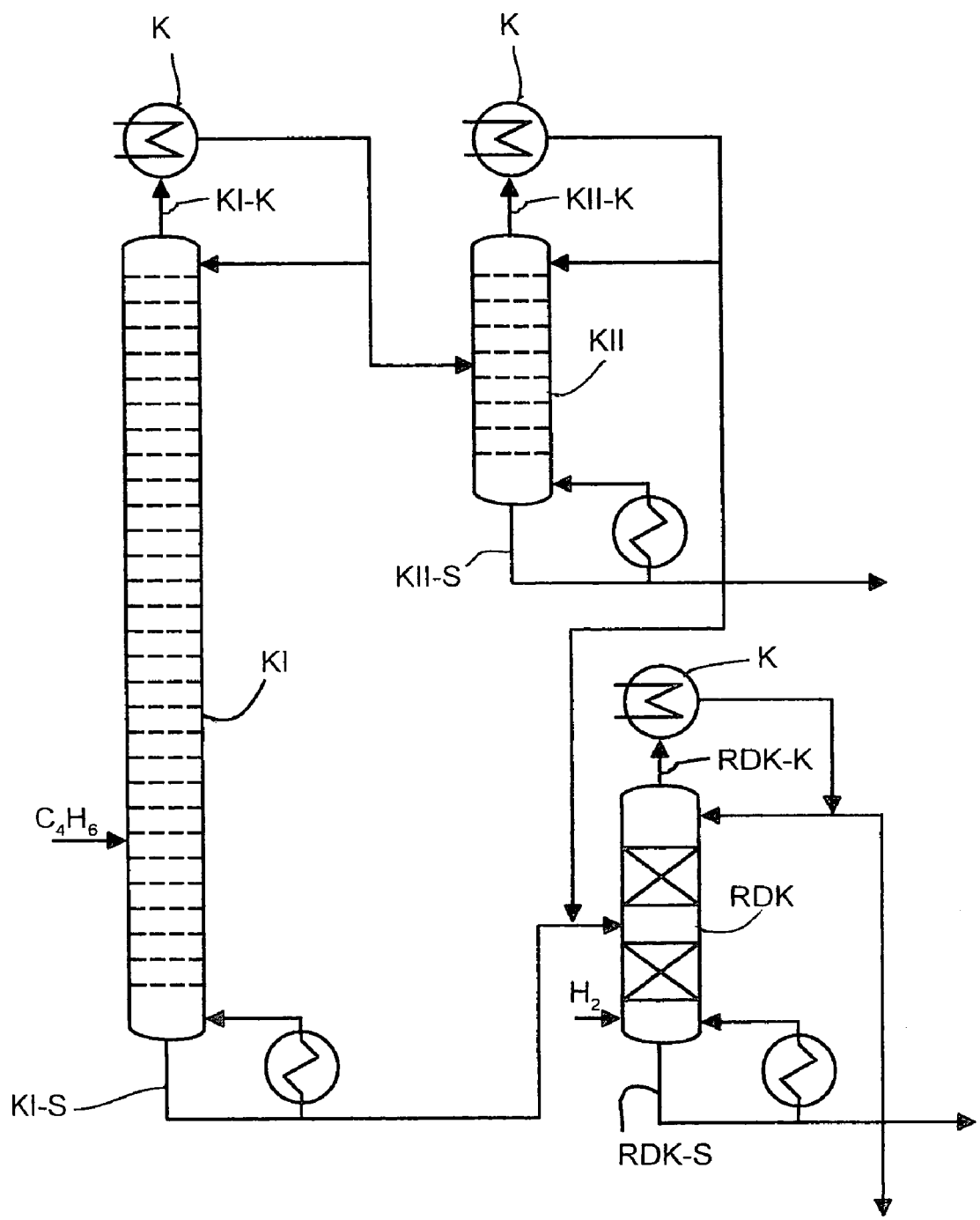

METHOD FOR WORKING UP CRUDE 1,3-BUTADIENE

The present invention relates to a process for working up a mixture of hydrocarbons obtained from a $C_4$ fraction by extractive distillation.

The term $C_4$ fraction refers to mixtures of hydrocarbons having predominantly 4 carbon atoms per molecule. $C_4$ fractions are obtained, for example, in the preparation of ethylene and/or propylene by thermal cracking, usually in steam crackers or FCC (Fluid Catalytic Cracking) plants, of a petroleum fraction such as liquefied petroleum gas, naphthal or gas oil. $C_4$ fractions are also obtained in the catalytic dehydrogenation of n-butane and/or n-butene. $C_4$ fractions generally comprise butanes, n-butene, isobutene, 1,3-butadiene together with small amounts of other hydrocarbons including butynes, in particular 1-butyne (ethylacetylene) and butenyne (vinylacetylene). The 1,3-butadiene content of $C_4$ fractions from steam crackers is generally from 10 to 80% by weight, preferably from 20 to 70% by weight, in particular from 30 to 60% by weight, while the content of vinylacetylene and ethylacetylene generally does not exceed 5% by weight.

The separation of $C_4$ fractions into their components is a complicated distillation problem because of the small differences in the relative volatilities of the components. The separation is therefore carried out by means of extractive distillation, i.e. distillation with addition of a selective solvent (also referred to as extractant) which has a boiling point higher than that of the mixture to be fractionated and increases the differences in the relative volatilities of the components to be separated from one another.

Many methods for the separation of $C_4$ fractions by means of extractive distillation using selective solvents are known. In all of them, the gaseous $C_4$ fraction which is to be separated into its components is brought into countercurrent contact with the liquid selective solvent under appropriate thermodynamic conditions, in general at low temperatures, frequently in the range from 20 to 80° C., and at moderate pressures, frequently from atmospheric pressure to 6 bar, so that the selective solvent is loaded with the components of the $C_4$ fraction for which it has a higher affinity, while the components for which the selective solvent has a lower affinity remain in the vapor phase and are taken off at the top. The components are subsequently fractionally liberated from the loaded stream of selective solvent in one or more further process steps under appropriate thermodynamic conditions, i.e. at a higher temperature and/or lower pressure than in the first process step.

The extractive distillation of $C_4$ fractions is frequently operated in such a way that the components of the $C_4$ fraction for which the selective solvent has a lower affinity than for 1,3-butadiene, in particular the butanes and the butenes, remain essentially in the gas phase while 1,3-butadiene and further hydrocarbons for which the selective solvent has a higher affinity than for 1,3-butadiene are virtually completely absorbed by the selective solvent. The gas phase is taken off at the top and is frequently referred to as raffinate 1. Such a process is described, for example, in DE-A 198 188 10, where the raffinate 1 is the stream denoted by Gbc in FIGS. 1 and 2 which is taken off at the top of the extractive distillation column E I.

The work-up of the selective solvent laden with 1,3-butadeine and further hydrocarbons for which the selective solvent has a higher affinity than for 1,3-butadiene is generally carried out by fractional desorption, with the hydrocarbons absorbed in the selective solvent being desorbed in the reverse order of their affinity for the selective solvent.

Such a process is described, for example, in DE-A 198 188 10, according to which the selective solvent which is laden with 1,3-butadiene and other $C_4$-hydrocarbons and is also referred to as extraction solution ad is, in a process step 3, transferred to a desorption zone which is at a lower pressure and/or higher temperature than the extraction zone and 1,3-butadiene is there desorbed from the extraction solution ad, with the major part of the other $C_4$-hydrocarbons remaining in the liquid phase. Two separate streams, namely 1,3-butadiene as crude 1,3-butadiene stream and the selective solvent laden with other $C_4$-hydrocarbons as extraction solution d, are taken off. Finally, the 1,3-butadiene still remaining in the extraction solution d and the other $C_4$-hydrocarbons are fractionally desorbed as at least two separate fractions in a second desorption zone which is at a lower pressure and/or elevated temperature than the first desorption zone and has a pressure and/or temperature gradient.

According to prevailing opinions, it has hitherto not been possible to separate the acetylenes and 1,2-butadiene from the crude 1,3-butadiene by distillation at justifiable cost. Particular problems were the small differences in the relative volatilities and the high reactivity of the components forming the crude 1,3-butadiene stream.

It is an object of the present invention to provide a process which makes it possible for acetylenes and 1,2-butadiene to be separated from a crude 1,3-butadiene stream by distillation at justifiable cost and at the same time ensures safe process operation. The process of the present invention thus makes it possible for crude 1,3-butadiene streams to be worked up by distillation without the costly upstream process step of extractive distillation using a selective solvent to separate off the acetylenes.

We have found that this object is achieved by a continuous process for separating a mixture of hydrocarbons which has been obtained by extractive distillation of a $C_4$ fraction using a selective solvent and comprises the hydrocarbons from the $C_4$ fraction which are more readily soluble in the selective solvent than are the butanes and the butenes, which comprises feeding the mixture into a first distillation column in which it is separated into a stream which is taken off at the top and comprises 1,3-butadiene, propyne, possibly further low boilers and possibly water and a bottom stream comprising 1,3-butadiene, 1,2-butadiene, acetylenes and possibly further high boilers, with the proportion of 1,3-butadiene in the bottom stream from the distillation column being regulated in such a way that it is at least sufficiently high to dilute the acetylenes to outside the range in which there is a risk of spontaneous decomposition, and passing the stream taken off from the top of the first distillation column to a second distillation column and separating it into a stream which is taken off at the top and comprises propyne, possibly further low boilers and possibly water and a bottom stream comprising pure 1,3-butadiene in the second distillation column.

Thus, according to the present invention, a crude 1,3-butadiene stream is subjected to a fractional distillation which is not sharp in respect of 1,3-butadiene in a distillation column and the acetylenes and 1,2-butadiene are taken off as a bottom stream which is diluted with 1,3-butadiene to outside the range in which there is a risk of spontaneous decomposition. Butadiene together with propyne, possibly further low boilers and possibly water are taken off at the top of the distillation column.

The stream from the top of the distillation column is preferably condensed in a condenser at the top of the column and part of the condensate is returned as runback to the column and the remainder is passed to a second distillation column in which it is separated into a stream which is taken off at the top and comprises propyne and possibly further low boilers and a bottom stream comprising pure 1,3-butadiene.

In both the above-described distillation columns, it is in principle possible to use all separation-active internals customary for butadiene distillations. Trays are particularly useful because they are easier to clean.

The composition of the crude 1,3-butadiene stream depends on the composition of the $C_4$ fraction which was fed to the extractive distillation and generally comprises all the acetylenes, all the 1,2-butadiene, from 30 to 70% of the cis-2-butene and at least 99% of the 1,3-butadiene from the $C_4$ fraction.

Here, the hydrocarbons having a boiling point lower than that of 1,3-butadiene are referred to as low boilers and the hydrocarbons having a boiling point higher than that of 1,3-butadiene are referred to as high boilers. A typical low boiler is propyne, and high boilers are predominantly hydrocarbons having a triple bond, hereinafter referred to as acetylenes, in particular 1-butyne (ethylacetylene) and butenyne (vinylacetylene).

The term "possibly" used here in the context of the composition of the streams obtained in the work-up by distillation means that the component(s) which is/are qualified in this way may be present in the respective streams depending on the specific process conditions, in particular the composition of the $C_4$ fraction used, the solvent used and/or auxiliaries used.

The separation of the acetylenes and 1,2-butadiene from the crude 1,3-butadiene by distillation is a complicated distillation problem because of the high reactivity of these components and because of the small differences in relative volatilities of the components forming the crude 1,3-butadiene stream. However, it has surprisingly been found that it is possible to separate off the acetylenes and 1,2-butadiene by distillation with a justifiable energy consumption and at the same time ensure process safety when the acetylenes and the 1,2-butadiene are taken off as bottom stream from a distillation column and are in this stream diluted with 1,3-butadiene to outside the range in which there is a risk of spontaneous decomposition. In general, dilution of the bottom stream to below 30 mol % of acetylenes is sufficient for this purpose. $C_4$ fractions generally have compositions in % by weight in the following ranges:

| | |
|---|---|
| 1,3-butadiene | from 10 to 80 |
| butenes | from 10 to 60 |
| butanes | from 5 to 40 |
| other $C_4$-hydrocarbons and other hydrocarbons, in particular | from 0.1 to 5 |
| $C_3$- and $C_5$-hydrocarbons | from 0 to not more than 5. |

In the present context, the term "pure 1,3-butadiene" refers to a stream having a 1,3-butadiene content of at least 99% by weight, preferably at least 99.6% by weight, with the balance being impurities, in particular 1,2-butadiene and cis-2-butene.

In a preferred process alternative, the bottom stream from the first distillation column and the stream from the top of the second distillation column are fed to a reactive distillation column in which a selective hydrogenation of the hydrocarbons containing triple bonds to hydrocarbons containing double bonds is carried out by means of hydrogen in the presence of a heterogeneous catalyst, with partial conversion of the acetylenes, to give a stream comprising 1,3-butadiene, butanes, butenes and hydrocarbons containing triple bonds which have not been hydrogenated at the top and a bottom stream comprising high boilers which is discharged.

In particular, vinylacetylene is selectively hydrogenated to the desired product 1,3-butadiene.

The stream from the top of the reactive distillation column or a substream thereof is preferably recycled to the extractive distillation column. However, it is also possible for the stream from the top of the reactive distillation column or a substream thereof to be taken from the plant and processed further in another way, for example by mixing into a cracker feed, or burnt.

The preferred process operation with selective hydrogenation of the acetylenes after the extractive distillation is advantageous from a process engineering point of view, in particular in respect of the choice of possible catalysts, since the selective hydrogenation is carried out in a process step in which virtually no selective solvent remains in the reaction mixture. In contrast, if the selective hydrogenation were, as in known processes, to be carried out in the extractive distillation column and thus in the presence of the selective solvent, the choice of catalyst would be considerably restricted by the selective solvent which can make the hydrogenation unselective. On the other hand, no such restrictions in respect of the choice of catalyst exist in the selective hydrogenation downstream of the extractive distillation.

The invention is illustrated below with the aid of a drawing and an example.

FIG. 1 schematically shows a plant for the fractionation of a crude 1,3-butadiene stream by distillation.

A crude 1,3-butadiene stream, designated as $C_4H_6$, is fed to a first distillation column K I in which it is separated into a stream K I-K taken off at the top and a bottom stream K I-S. The stream K I-K from the top is condensed in a condenser K at the top of the column, part of the condensate is returned as runback to the column and the remainder is taken off and fed to a second distillation column K II. The bottom stream K I-S is taken off and fed to a reactive distillation column RDK.

In the second distillation column K II, the condensate from the column K I is fractionated to give a stream K II-K which is taken off at the top and condensed in a condenser K, and part of the condensate is returned as runback to the column and the remainder is fed to the reactive distillation column RDK. The bottom stream K II-S from the second distillation column K II is taken off as pure 1,3-butadiene stream.

In the reactive distillation column RDK, the hydrocarbons containing triple bonds are selectively hydrogenated to hydrocarbons containing double bonds by means of hydrogen in the presence of a heterogeneous catalyst. A stream RDK-K is taken off at the top, condensed in a condenser K, part of the condensate is returned to the reactive distillation column RDK and the remainder is preferably, as shown in the figure, recycled to the extractive distillation column.

The bottom stream from the reactive distillation column, viz. stream RDK-S, which comprises predominantly high boilers, is discharged from the plant and preferably burnt.

EXAMPLE

Work-Up of Crude 1,3-butadiene by Distillation

A crude 1,3-butadiene stream, $C_4H_6$, which had been obtained from a $C_4$ fraction by extractive distillation was fed to a distillation column having 80 theoretical plates on the 25th plate, counting the theoretical plates from the bottom upward. The crude 1,3-butadiene stream $C_4H_6$ had the following composition in % by weight:

| | |
|---|---|
| Propyne | 0.11 |
| 1,3-butadiene | 98.58 |
| 1,2-butadiene | 0.30 |
| 1-butyne | 0.30 |
| vinylacetylene | 0.56 |
| water | 0.15. |

In the first distillation column K I, the feed stream was separated into a stream K I-K which was taken off at the top and had the following composition in % by weight:

| | |
|---|---|
| Propyne | 0.11 |
| 1,3-butadiene | 99.73 |
| water | 0.16 | and a bottom stream K I-S having the following composition in % by weight:

| | |
|---|---|
| cis-2-butene | 0.52 |
| 1,3-butadiene | 40.0 |
| 1,2-butadiene | 15.1 |
| 1-butyne | 13.75 |
| vinylacetylene | 29.17 |
| 3-methyl-1-butene | 0.98 |
| 2-methyl-2-butene | 0.48. |

The stream K I-K from the top of the first distillation column K I was divided into an output stream (1/7 of the stream K I-K) and a runback stream (6/7 of the stream K I-K). The output stream was fed to a second distillation column K II having 25 theoretical plates on the 14th theoretical plate and separated into a stream K II-K which was taken off at the top and had the following composition in % by weight:

| | |
|---|---|
| Propyne | 79.52 |
| 1,3-butadiene | 20.0 and |
| water | 0.48 | and a bottom stream K II-S comprising pure 1,3-butadiene and having a 1,3-butadiene content of 99.99%. The bottom stream K II-S was taken off as desired product.

Compared to a known process for recovering 1,3-butadiene from a $C_4$ fraction with separation of the acetylenes from 1,3-butadiene by extractive distillation using a selective solvent, the present process achieved an energy saving of about 9%. Furthermore, the plant could be simplified by omission of the column for the separation of acetylenes from 1,3-butadiene by extractive distillation, with a corresponding reduction in the capital costs and the space requirement.

We claim:

1. A continuous process for separating a mixture of hydrocarbons which has been obtained by extractive distillation of a $C_4$ fraction using a selective solvent and the hydrocarbons from the $C_4$ fraction which are more readily soluble in the selective solvent than are the butanes and the butenes, which comprises feeding the mixture into a first distillation column in which it is separated into a stream which is taken off at the top and comprises 1,3-butadiene and propyne, and a bottom stream comprising 1,3-butadiene, 1,2-butadiene and acetylenes, with the proportion of 1,3-butadiene in the bottom stream from the first distillation column being regulated in such a way that it is at least sufficiently high to dilute the acetylenes to outside the range in which there is a risk of spontaneous decomposition, and passing the stream taken off from the top of the first distillation column to a second distillation column and separating it into a stream which is taken off at the top and comprises propyne, and a bottom stream comprising pure 1,3-butadiene in the second distillation column.

2. The process as claimed in claim 1 wherein the proportion of 1,3-butadiene in the bottom stream from the first distillation column is regulated in such a way that the proportion of acetylenes in the bottom stream is less than 30 mol %.

3. The process as claimed in claim 1 wherein the bottom stream from the first distillation column and the stream from the top of the second distillation column are fed to a reactive distillation column in which a selective hydrogenation of the hydrocarbons containing triple bonds to hydrocarbons containing double bonds is carried out by means of hydrogen in the presence of a heterogeneous catalyst, with partial conversion of the acetylenes, to give a stream comprising 1,3-butadiene, butanes, butenes and hydrocarbons containing triple bonds which have not been hydrogenated at the top and a bottom stream comprising high boilers which is discharged.

4. The process as claimed in claim 3, wherein the stream taken off at the top of the reactive distillation column or a substream thereof is recycled to the extractive distillation.

\* \* \* \* \*